(12) United States Patent
Albers et al.

(10) Patent No.: US 10,228,725 B2
(45) Date of Patent: Mar. 12, 2019

(54) FLEXIBLE BAND WEARABLE ELECTRONIC DEVICE

(71) Applicant: Intel IP Corporation, Santa Clara, CA (US)

(72) Inventors: Sven Albers, Regensburg (DE); Klaus Reingruber, Langquaid (DE); Andreas Wolter, Regensburg (DE); Georg Seidemann, Landshut (DE); Christian Geissler, Teugn (DE); Thorsten Meyer, Regensburg (DE); Gerald Ofner, Regensburg (DE)

(73) Assignee: Intel IP Corporation, Santa Clara, CA (US)

( * ) Notice: Subject to any disclaimer, the term of this patent is extended or adjusted under 35 U.S.C. 154(b) by 122 days.

(21) Appl. No.: 15/282,633

(22) Filed: Sep. 30, 2016

(65) Prior Publication Data

US 2018/0092443 A1    Apr. 5, 2018

(51) Int. Cl.
   *A44C 5/00* (2006.01)
   *A44C 5/02* (2006.01)
   (Continued)

(52) U.S. Cl.
   CPC ............ *G06F 1/163* (2013.01); *A44C 5/00* (2013.01); *A44C 5/02* (2013.01); *A44C 5/105* (2013.01);
   (Continued)

(58) Field of Classification Search
   CPC ...... G04B 37/1486; G04B 37/16; A44C 5/00; A44C 5/0007; A44C 5/0015; A44C 5/0053; A44C 5/0061
   See application file for complete search history.

(56) References Cited

U.S. PATENT DOCUMENTS

| 4,115,904 A | * | 9/1978 | Zwyssig | A44C 5/2052 24/19 |
| 4,554,783 A | * | 11/1985 | Yokoyama | A44C 5/102 59/82 |

(Continued)

FOREIGN PATENT DOCUMENTS

| EP | 0165206 A1 * | 12/1985 | ............... A44C 5/10 |
| WO | 2018063530 | 4/2018 | |

OTHER PUBLICATIONS

Lenherr, Jean-Claude, English Translation of EP 0165206, originally published Dec. 18, 1985, full document.*

(Continued)

*Primary Examiner* — Daniel P Wicklund

(74) *Attorney, Agent, or Firm* — Schwegman Lundberg & Woessner, P.A.

(57) ABSTRACT

A flexible band wearable electronic device includes a plurality of rigid links. The flexible band wearable electronic device also includes a number of pivot joints coupling the plurality of rigid links together. The flexible band wearable electronic device further includes a first electronic device on a first of the plurality of rigid links, and a second electronic device on a second of the plurality of rigid links. The flexible band wearable electronic device still further includes an electrical communication pathway between first electronic device and the second electronic device and through at least a portion of one of the number of pivot joints.

18 Claims, 7 Drawing Sheets

(51) Int. Cl.

| | | |
|---|---|---|
| *A44C 5/10* | (2006.01) | |
| *A45F 5/00* | (2006.01) | |
| *A61B 5/00* | (2006.01) | |
| *A61B 5/11* | (2006.01) | |
| *G06F 1/16* | (2006.01) | |
| *A61B 5/021* | (2006.01) | |
| *A61B 5/024* | (2006.01) | |
| *G04B 37/14* | (2006.01) | |
| *G04B 47/00* | (2006.01) | |
| *A61B 5/0205* | (2006.01) | |
| *H04B 1/3827* | (2015.01) | |

(52) U.S. Cl.
CPC ............ *A45F 5/00* (2013.01); *A61B 5/02055* (2013.01); *A61B 5/681* (2013.01); *G04B 37/1486* (2013.01); *G04B 47/00* (2013.01); *H04B 1/385* (2013.01); *A45F 2005/008* (2013.01); *A45F 2200/0508* (2013.01); *A61B 5/021* (2013.01); *A61B 5/02438* (2013.01); *A61B 5/1112* (2013.01); *A61B 2560/0257* (2013.01); *A61B 2560/0443* (2013.01); *A61B 2562/0219* (2013.01)

(56) References Cited

U.S. PATENT DOCUMENTS

| | | | | |
|---|---|---|---|---|
| 2004/0224223 | A1* | 11/2004 | Sun | H01M 2/1061 429/127 |
| 2006/0236505 | A1* | 10/2006 | Maatta | G06F 1/1681 16/366 |
| 2007/0158376 | A1* | 7/2007 | Radley-Smith | A44C 5/0007 224/219 |
| 2010/0219943 | A1 | 9/2010 | Vanska et al. | |
| 2012/0182677 | A1* | 7/2012 | Seo | H04B 1/385 361/679.01 |
| 2013/0107674 | A1 | 5/2013 | Gossweiler, III et al. | |
| 2014/0313128 | A1 | 10/2014 | Golko et al. | |
| 2015/0124566 | A1 | 5/2015 | Lake et al. | |
| 2015/0223574 | A1* | 8/2015 | Nakamura | A44C 5/0053 224/181 |
| 2015/0361696 | A1* | 12/2015 | Tazbaz | G06F 1/1652 361/679.27 |
| 2015/0366089 | A1* | 12/2015 | Park | G06F 1/1641 361/679.01 |
| 2016/0077548 | A1* | 3/2016 | Lim | G06F 1/166 361/679.26 |
| 2016/0094259 | A1* | 3/2016 | Hatanaka | A44C 5/00 455/90.2 |
| 2016/0151669 | A1* | 6/2016 | Komulainen | A44C 5/105 702/160 |
| 2017/0000222 | A1* | 1/2017 | Lee | G04G 17/06 |
| 2017/0023985 | A1* | 1/2017 | Xin | G06F 1/1681 |
| 2017/0086537 | A1* | 3/2017 | De Iuliis | G04B 37/1486 |
| 2017/0188668 | A1* | 7/2017 | Watterson | G04B 47/063 |

OTHER PUBLICATIONS

"International Application Serial No. PCT/US2017/046469, International Search Report dated Nov. 23, 2017", 3 pgs.

"International Application Serial No. PCT/US2017/046469, Written Opinion dated Nov. 23, 2017", 6 pgs.

* cited by examiner ably sized and shaped. In another example, the plurality of

FLEXIBLE BAND WEARABLE ELECTRONIC DEVICE

BACKGROUND

Jewelry, specifically watches, typically will have a bracelet or a band to secure the piece of jewelry to the user's person. Manufacturers have been increasing the utility and functionality of jewelry, specifically watches, by adding additional electronics to make the jewelry "smart". Rigid printed circuit boards do not allow for deformation of the printed circuit boards. Flexible printed circuit boards can be cost-prohibitive.

OVERVIEW

The present inventors have recognized, among other things, that a problem to be solved can include a limited ability to alter the functionality of existing wearable electronic devices. The present inventors have also recognized, among other things, that a problem to be solved can include reducing the size of wearable electronic devices. The present inventors have also recognized, among other things, that a problem to be solved can include providing a flexible coupling of electronic devices. The present subject matter can help provide a solution to this problem, such as by coupling, or integrating, electronic devices with rigid links in a flexible band.

A flexible band wearable electronic device includes a plurality of rigid links. The flexible band wearable electronic device also includes a number of pivot joints coupling the plurality of rigid links together. The flexible band wearable electronic device further includes a first electronic device on a first of the plurality of rigid links, and a second electronic device on a second of the plurality of rigid links. The flexible band wearable electronic device still further includes an electrical communication pathway between first electronic device and the second electronic device and through at least a portion of one of the number of pivot joints.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
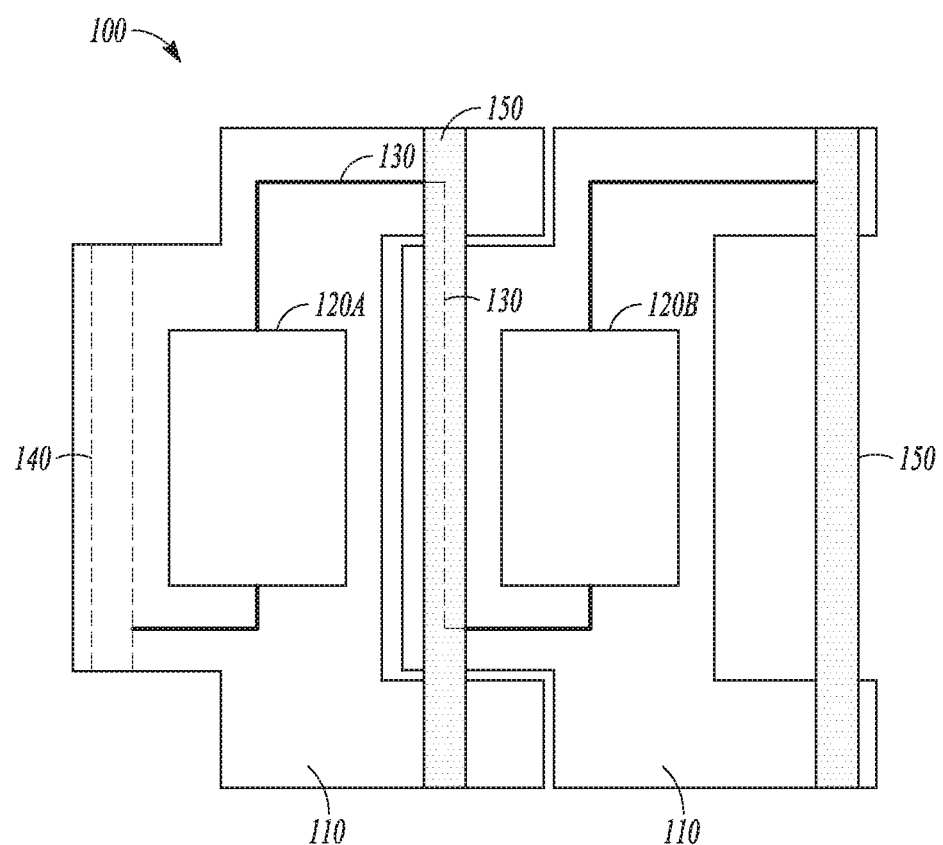
FIG. 1 illustrates a view of one example of a portion of a flexible band wearable electronic device in accordance with some embodiments of the invention.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims FIG. 1 illustrates a view of one example of a portion of a flexible band wearable electronic device 100 ("wearable device 100") in accordance with some embodiments of the invention. The wearable device 100 can include a plurality of rigid links 110, a first electronic device 120A, a second electronic device 120B, an electrical communication pathway 130, a cylindrical passage 140, and a connector 150. In one example, the plurality of rigid links 110 can be identically sized and shaped. In another example, the plurality of rigid links 110 can be substantially similar in size and shape. In yet another example, the plurality of rigid links 110 can be substantially different in size and shape, yet still interconnect such that a substantially continuous chain of links is formed. The plurality of rigid links 110 can be components of a piece of jewelry. The plurality of rigid links 110 can be components of a watch.

The first and second electronic devices 120A, B can be coupled to the plurality of rigid links 110. The first and second electronic devices 120A, B and the plurality of rigid links 110 can be coupled to the electrical communication pathway 130 such that the electrical communication pathway 130 is able to transmit one or more electrical signals. The electrical signals can be either analog or digital.

The insertion of connector 150 into cylindrical passage 140 can create a pivot joint that physically couples the plurality of rigid links 110 together. Additionally, the insertion of connector 150 into cylindrical passage 140 can create a pivot joint that rotatably couples the plurality of rigid links 110 together. Further, the insertion of connector 150 into the cylindrical passage 140 can also establish the electrical communication pathway 130 between the plurality of rigid links 110. The insertion of connector 150 into the cylindrical passage 140 establishes the electrical communication pathway 130 between the plurality of rigid links 110 by completing one or more electrical circuits between the plurality of rigid links 110.

Figure 2:
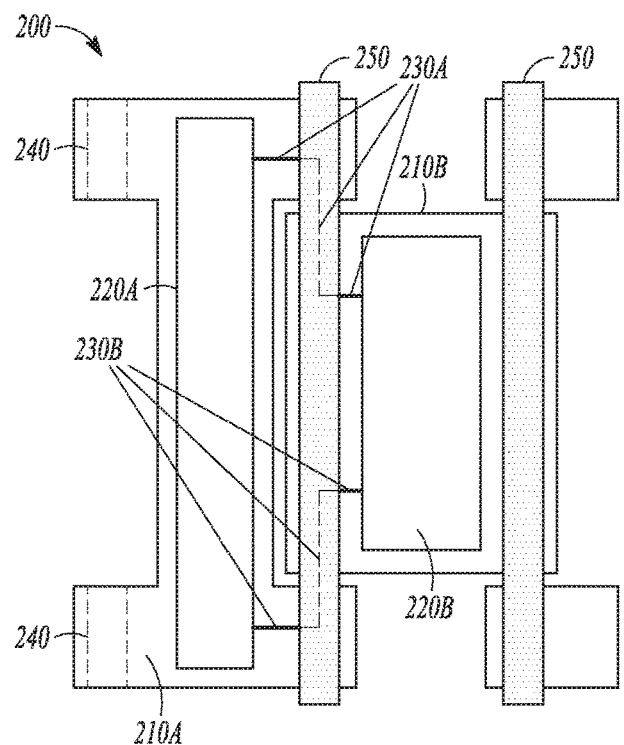
FIG. 2 illustrates a view of another example of a portion of a flexible band wearable electronic device in accordance with some embodiments of the invention.

FIG. 2 illustrates a view of another example of a portion of a flexible band wearable electronic device 200 ("wearable device 200") in accordance with some embodiments of the invention. The wearable device 200 can include a first rigid link 210A, a second rigid link 210B, a first electronic device 220A, a second electronic device 220B, an electrical communication pathway 230, a cylindrical passage 240, and a connector 250. The first rigid link 210A can be sized and shaped in a substantially different way than the second rigid link 210B. However, the first and second rigid links 210A, B can be sized and shaped such that they are able to interconnect with each other. The interconnection of the first and second rigid links 210A, B can align cylindrical passages (e.g., cylindrical passage 240) such that a connector (e.g., connector 250) can be inserted into the cylindrical passages.

In one example, the insertion of connector 250 into the aligned cylindrical passages can physically couple the first and second rigid links 210A, B together. The insertion of connector 250 into the aligned cylindrical passages can rotatably couple the first and second rigid links 210A, B together. A substantially continuous chain of rigid links can be formed by coupling a plurality of first and second rigid links 210A, B together.

In another example, the insertion of connector 250 into the aligned cylindrical passages can further establish the electrical communication pathway 230. The insertion of connector 250 into the cylindrical passages can further establish the electrical communication pathway 130 by completing one or more electrical circuits between the first rigid link 210A and the second rigid link 210B.

Figure 3:
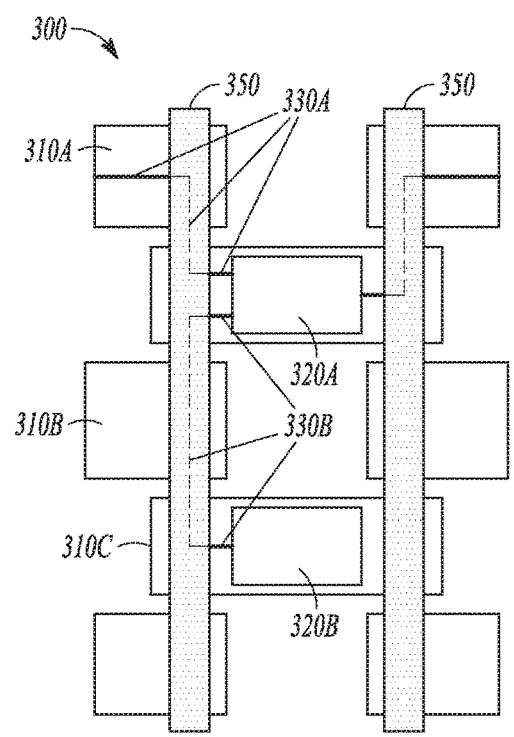
FIG. 3 illustrates a view of yet another example of a portion of a flexible band wearable electronic device in accordance with some embodiments of the invention.

FIG. 3 illustrates a view of yet another example of a portion of a flexible band wearable electronic device 300 ("wearable device 300") in accordance with some embodiments of the invention. The wearable device 300 can include a first rigid link 310A, a second rigid link 310B, a third rigid link 310C, a first electronic device 320A, a second electronic device 220B, an electrical communication pathway 330A, an electrical communication pathway 330B, and a connector 350. The first, second, and third rigid links 310A, B, C can be sized and shaped in a substantially different way from one another. However, the first, second, and third rigid links 310A-C can be sized and shaped such that they are able to interconnect with one another. The interconnection of the first, second, and third rigid links 310A-C can align cylindrical passages (not shown) such that a connector connector 350) can be inserted into the cylindrical passages.

In one example, the insertion of connector 350 into the aligned cylindrical passages can physically couple the first, second, and third rigid links 310A-C together. The insertion of connector 250 into the aligned cylindrical passages can rotatably couple the first, second, and third rigid links 310A-C together. A substantially continuous chain of links can be formed by coupling a plurality of first, second, and third rigid links 310A-C together.

In another example, the insertion of connector 350 into the aligned cylindrical passages can establish one or more electrical communication pathways (e.g., electrical communication pathways 330A, B). The one or more electrical communication pathways can transmit one or more electrical signals between electronic devices (e.g., electronic devices 320A, B). The connector 350 can have one or more electrically isolated conductors for establishing the one or more electrical communication pathways. The connector 350 can be a fastener, splint, shim, or the like. The connector 350 can be constructed by alternating electrically conductive and non-conductive material segments to create electrically isolated conductors. The electronic devices can be located within the same segment of a plurality of rigid links such that the electrical signals being transmitted by the electrical communication pathway (e.g., electrical communication pathway 320B) are only transmitted over one connector 350. In yet another example, the first electronic device 320A and the second electronic device 320B can be sub-components of an electronic system. The sub-components of the electronic system can be in either electrical or wireless communication.

Figure 4:
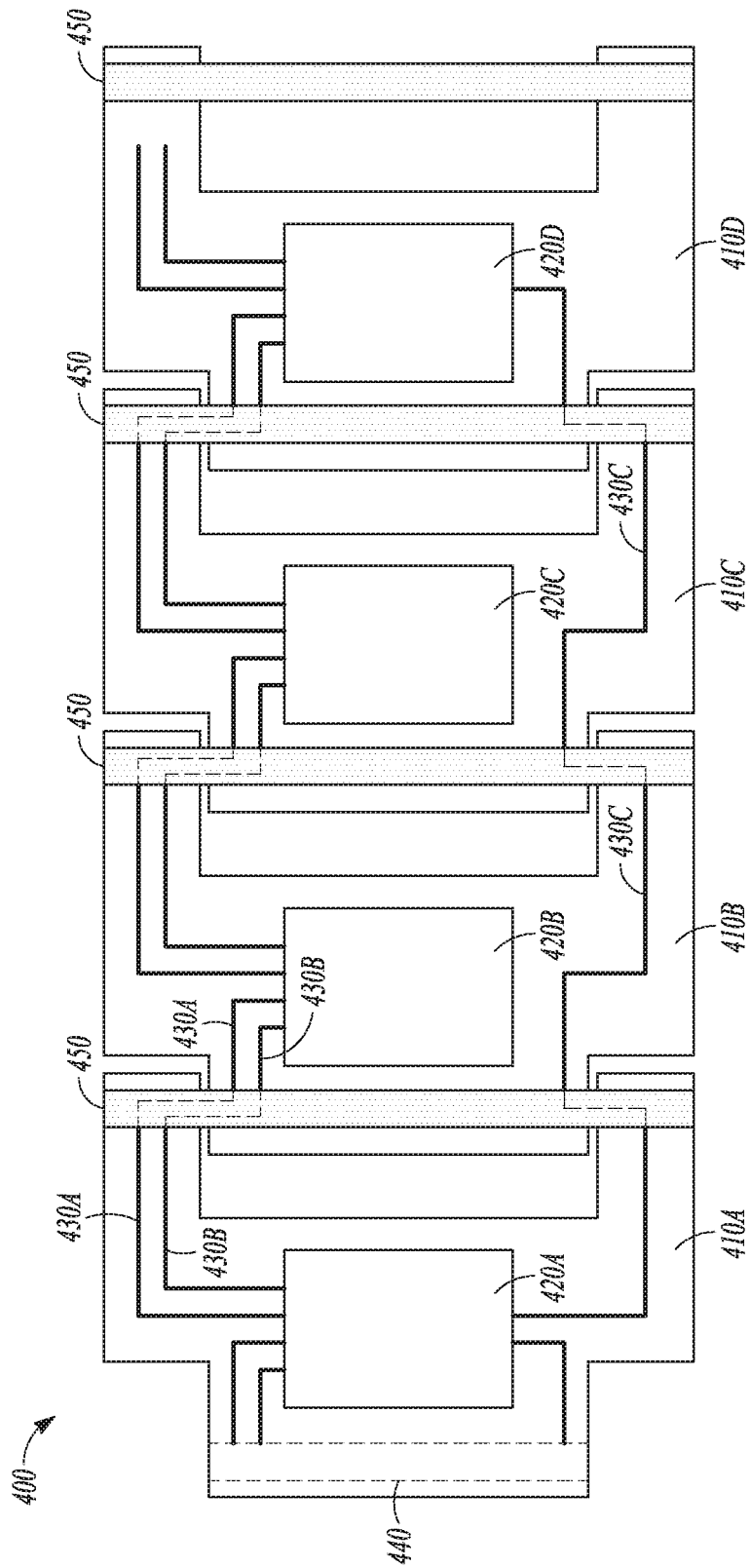
FIG. 4 illustrates another view of a portion of the flexible band wearable electronic device of FIG. 1.

FIG. 4 illustrates another view of a portion of the flexible band wearable electronic device 400 ("wearable device 400") of FIG. 1. The wearable device 400 can include a plurality of rigid links 410A-D, electronic devices 120A-D, electrical communication pathways 130A-B, a cylindrical passage 440, and a connector 450. As previously discussed herein, the reception of the connector 450 within the cylindrical passage can physically or rotatably couple (e.g., create a pivot joint between) the plurality of rigid links 410A-D, or establish one or more communication pathways 430A-C. In one example, an electrical communication pathway (e.g., electrical communication pathway 430A, B) can be established through at least a portion of one of the number of pivot joints (e.g., the electrical communication pathway can be established through one connector 450). In another example, an electrical communication pathway (e.g., electrical communication pathway 430C) can be established through at least a portion of a number of pivot joints (e.g., the electrical communication pathway can be established through one or more connectors 450). The establishment of an electrical communication pathway (e.g., electrical communication pathway 430C) through one or more connectors 450 can allow for one or more rigid links (e.g., second and third rigid links 410B, C) to transmit one or more electrical signals between electronic devices coupled to other rigid links (e.g., first and fourth rigid links 410A. The establishment of an electrical communication pathway (e.g., electrical communication pathway 430C) through one or more connectors 450 can allow for an electronic device (e.g., electronic device 420A) to electrically communicate with another electronic device (e.g., electronic device 420D) despite the electronic devices being coupled to rigid links that are not physically adjacent to each other (e.g., rigid links 410A, D).

Figure 5:
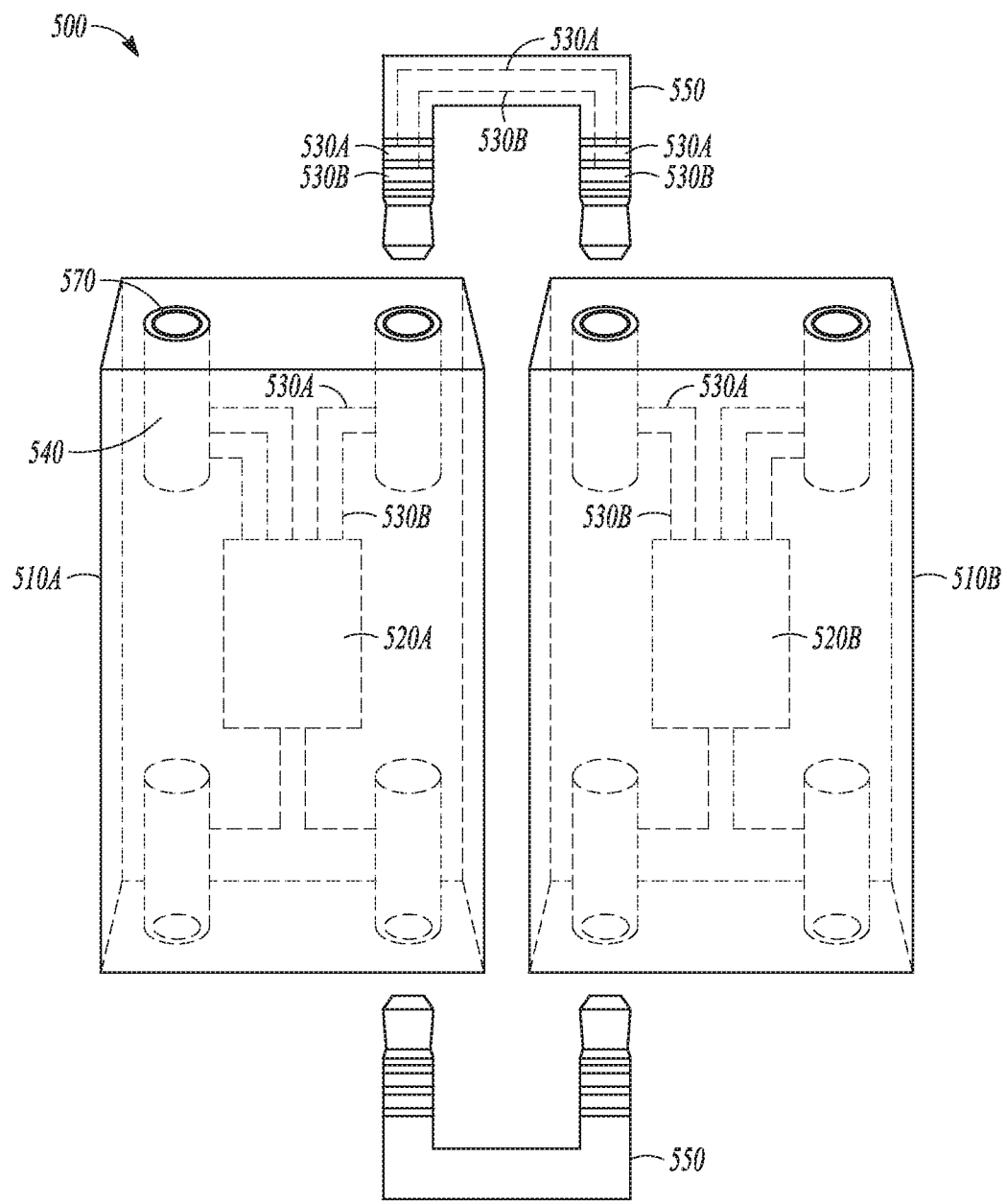
FIG. 5 illustrates a view of still yet another example of a portion of a flexible band wearable electronic device in accordance with some embodiments of the invention.

FIG. 5 illustrates a view of still yet another example of a portion of a flexible band wearable electronic device 500 ("wearable device 500") in accordance with some embodiments of the invention. The wearable device 500 can include a first rigid link 510A, a second rigid link 510B, a first electronic device 520A, a second electronic device 520B, communication pathways 530A-B, cylindrical passages 540, and connector 550. In an example, the first and second rigid link 510A, B can be physically or rotatably coupled through use of the connector such that the first electronic device and the second electronic device are in electrical communication via the electrical communication pathways 530A-B. The connector 550 can be any type of connector that allows for one or more electrical signals to be transmitted through the connector 550 (e.g., has one or more conductors). The connector 550 can be a connector with one or more electrically isolated channels (e.g., communication pathways) that allow for one or more electrical signals to be transmitted without interference from other electrical signals being transmitted on other electrically isolated channels. In an example, the connector 550 can be a 3.5 mm headphone-type connector.

The wearable device 500 can include a seal 570 that is coupled with the cylindrical passages 550. The seal 570 can provide an interference fit with the connector 550 when the seal 570 is coupled with the connector (e.g., when a user or manufacturer inserts the connector 550 into the cylindrical passage 540). The seal 570 can be an o-ring, gasket, or the like.

The wearable device 500 can include one or more electronic devices (e.g., first or second electronic device 520A, B). The one or more electronic devices can include a printed circuit board. The one or more electronic devices can be selected from the group consisting of a processor, battery, accelerometer, gyroscope, inertial measurement unit, global positioning system receiver, cellular radio, Bluetooth radio, WiFi radio, solid state memory, random access memory, microphone, speaker, induction coil, heart rate sensor, blood pressure sensor, temperature sensor, barometric pressure sensor, photosensor, liquid sensor, diode, and a display.

Additionally, the one or more electronic devices can allow for wireless communication. The one or more electronic devices (e.g., first or second electronic device 520A, B) can be in wireless communication with each other. Wireless communication can be achieved by transmitting electromagnetic energy (e.g., radio waves), representative of analog or digital electrical signals through a medium (e.g., air). The wireless communication can utilize one or more standardized forms of wireless communication such as the IEEE 802.11 (Wi-Fi) standards, Bluetooth Core Specification versions 1.0-4.2, or cellular networks (e.g., GSM, CDMA, GPRS, EDGE, AMPS, or LTE), but is not so limited.

Figure 6A:
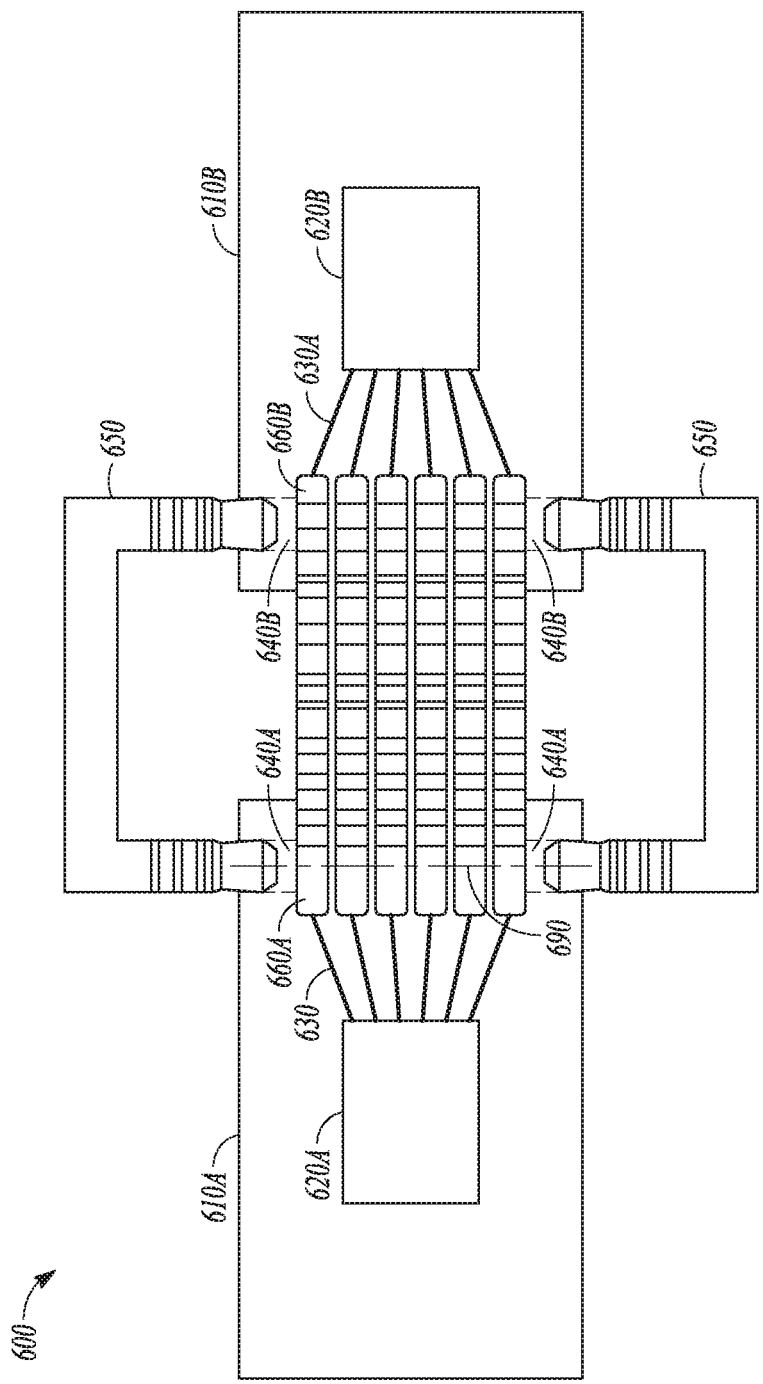
FIG. 6A illustrates a view of an additional example of a portion of a flexible band wearable electronic device in accordance with some embodiments of the invention.

FIG. 6A illustrates a view of an additional example of a portion of a flexible band wearable electronic device 600 ("wearable device 600") in accordance with some embodiments of the invention. The wearable device 600 can include a first rigid link 610A, a second rigid link 610B, a first electronic device 620A, a second electronic device 620B, a communication pathway 630, a cylindrical passage 640A, a cylindrical passage 640B, a connector 650, and one or more electrically conductive gears 660A, B.

The one or more electrically conductive gears 660A, B can be coupled to the first and second rigid link 610A, B. In an example, one or more first (left) electrically conductive gears (e.g., electrically conductive gear 660A) can be coupled to the first rigid link 610A. One or more second (right) electrically conductive gears (e.g., electrically conductive gear 660B) can be coupled to the second rigid link 610B. The first and second electrically conductive gears can be in communication with each other. The first and second electrically conductive gears can be physically engaged (e.g., intermeshed) with each other. In another example, the one or more electrically conductive gears 660A, B can differ in size, shape, or number of teeth, but will still be sized and shaped to intermesh with each other such that an electrical signal can be transmitted through the intermeshed one or more electrically conductive gears 660A, B. In yet another example, the one or more electrically conductive gears 660A, B can be only a portion of a complete gear (e.g., a quarter, a third, or half of a complete gear wheel).

Additionally, the one or more electrically conductive gears 660A, B can be in electrical communication with the communication pathway 630. The coupling together of the first rigid link 610A with the second rigid link 610B can result in the one or more first electrically conductive gears (e.g., electrically conductive gear 660A) physically engaging with the one or more second electrically conductive gears (e.g., electrically conductive gear 660B). The physical engagement (e.g., intermeshing) of the one or more electrically conductive gears 630A, B can establish the electrical communication pathway 630 between the first electronic device 620A and the second electronic device 620B. It is anticipated by the present subject matter that more than one set of electrically conductive gears can be used to establish more than one electrical communication pathway. In an example, the one or more electrically conductive gears (e.g., electrically conductive gear 660A) of the first rigid link 610A can each be electrically isolated from the other electrically conductive gears that are also coupled to the first rigid link 610A.

Further, each electrically conductive gear (e.g., electrically conductive gear 660A) can have a central gear axis (shown in FIG. 6B as feature 680) about which the gear is allowed to rotate. In an example, the cylindrical passage 640A can have a central passage axis 690 that is collinear with the central gear axis (denoted in FIG. 6B as feature 680). The first and second rigid links 610A, B can be physically coupled together through the reception of the connector 650 into the cylindrical passages 640A, B. Additionally, the reception of the connector 650 into the cylindrical passages 640A, B can create further electrical communication pathways between the first and second electronic devices 620A, B.

Figure 6B:
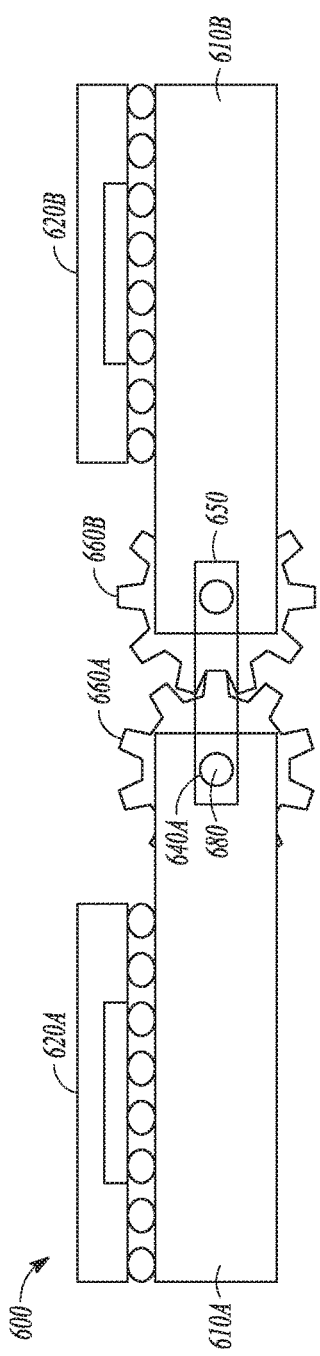
FIG. 6B illustrates another view of the flexible band wearable electronic device of FIG. 6A.

FIG. 6B illustrates another view of the flexible band wearable electronic device 600 ("wearable device 600") of FIG. 6A in an unbent configuration. The wearable device 600 can include a first rigid link 610A, a second rigid link 610B, a first electronic device 620A, a second electronic device 620B, a cylindrical passage 640A, a connector 650, one or more electrically conductive gears 660A, B, and a central gear axis 680. As previously discussed with reference to FIG. 6A, each of the one or more electrically conductive gears (e.g., electrically conductive gear 660A) can have a central gear axis 680. The central gear axis 680 and the central passage axis 690 can be collinear. The central gear axis 680 extends perpendicular from the page from the perspective of the viewer.

In an example with the central gear axis 680 and the central passage axis 690 being collinear, the first rigid link 610A and the second rigid link 620A are able to rotate about a pivot joint (formed collectively, in part, by the cylindrical passages 640A,B; the connector 650; and the one or more electrically conductive gears 660A, B). The formation of the pivot joint can establish an electrical communication pathway (e.g., electrical communication pathway 630) between the first and second rigid links 610A, B. The formation of the pivot joint can allow for the electrical communication of electronic devices 620A, B while also allowing the first rigid link to rotate freely about the pivot joint. The formation of the aforementioned pivot point can also allow for electrical systems to be distributed across the plurality of rigid links such that the footprint of the electrical system is reduced. Additionally, the formation of the aforementioned pivot point can allow for a flexible and resilient connection between one or more electronic devices.

Figure 6C:
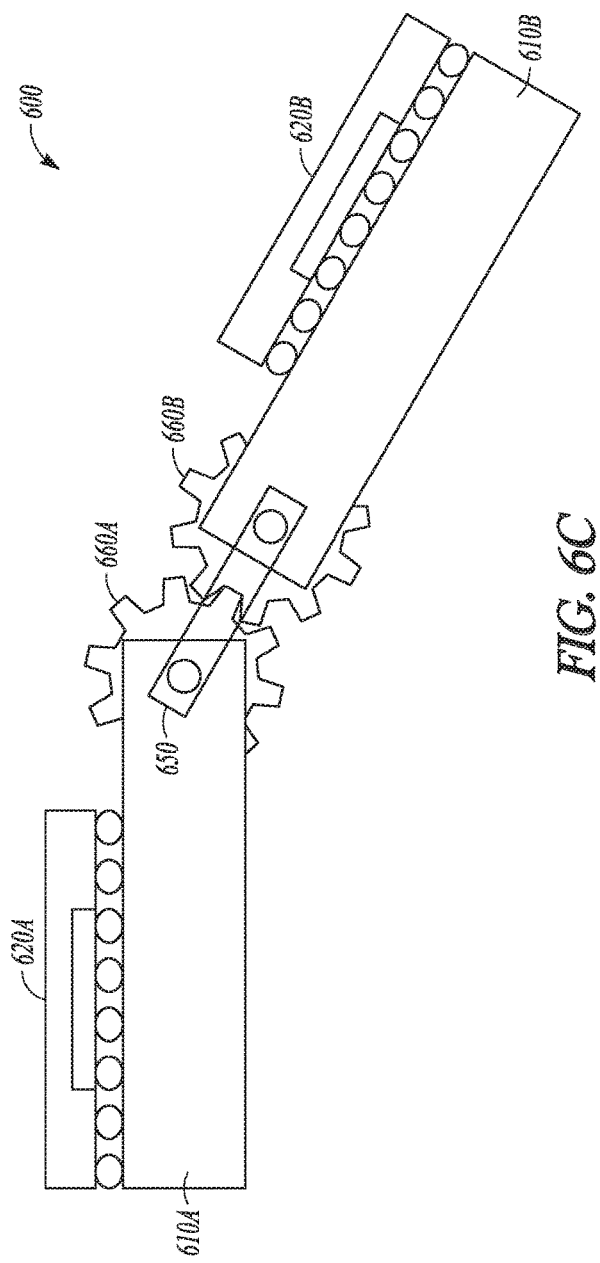
FIG. 6C illustrates yet another view of the flexible band wearable electronic device of FIG. 6A.

FIG. 6C illustrates a view of the flexible band wearable electronic device of FIG. 6A in a bent configuration. FIG. 6C shows that the formation of a pivot joint allows for the second rigid link 610B to be moved (e.g., deflected or rotated) with respect to the first rigid link 610A while also maintaining an electrical communication pathway (e.g., electrical communication pathway 630). The electrical communication is less likely to fatigue or decay with repeated movement of the first and second rigid links 610A, B. Fatigue and decay are reduced by providing electrically conductive pivot joints that facilitate electrical communication between the plurality of rigid links (e.g., first and second rigid links 610A, B). The pivot joints can be more resilient than a rigid or flexible printed circuit board.

Figure 7:
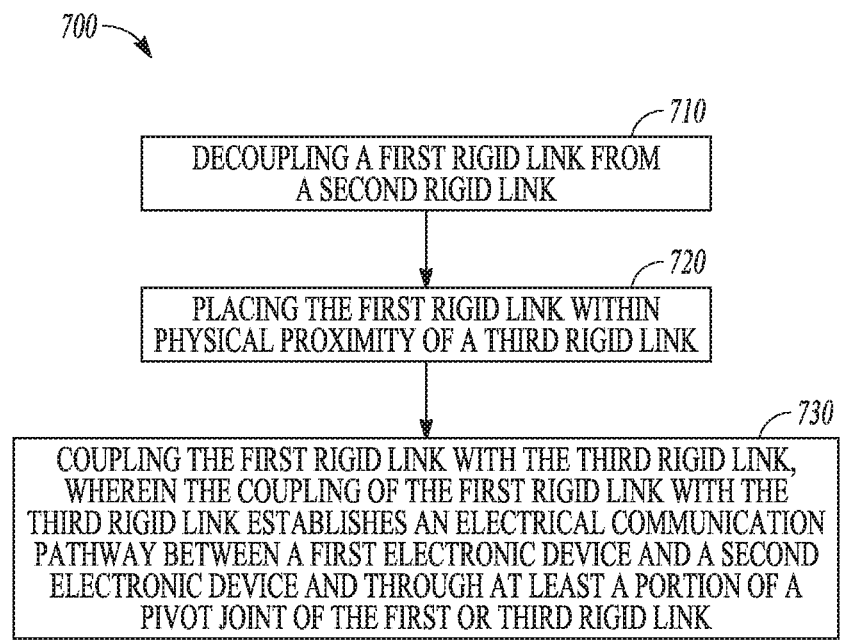
FIG. 7 is a block diagram of a method for modifying a wearable electronic device 700.

FIG. 7 is a block diagram of a method for modifying a wearable electronic device 700. Operation 710 can include decoupling a first rigid link (e.g., first rigid link 410A) from a second rigid link (e.g., second rigid link 410B). Operation

720 can include placing the first rigid link within physical proximity of a third rigid link (e.g., third rigid link 410C). Operation 730 can include coupling the first rigid link with the third rigid link, wherein the coupling of the first rigid link with the third rigid link establishes an electrical communication pathway (e.g., electrical communication pathway 430A) between a first electronic device (e.g., first electronic device 420A) and a second electronic device (e.g., second electronic device 420B) and through at least a portion of a pivot joint (e.g., the reception of the connector 450 within the cylindrical passage 440) of the first or third rigid link.

Additionally, the method for modifying a wearable electronic device 900 can include that the third rigid link is a replacement for the second rigid link. Further, the method for modifying a wearable electronic device 900 can include that third rigid link is added to increase functionality of the wearable electronic device. Still further, the method for modifying a wearable electronic device 900 can include that the coupling of the first rigid link with the third rigid link also includes intermeshing one or more electrically conductive gears of the first rigid link with one or more electrically conductive gears of the third rigid link.

VARIOUS NOTES & EXAMPLES

Example 1 can include or use a flexible band wearable electronic device, comprising a plurality of rigid links; a number of pivot joints coupling the plurality of rigid links together; a first electronic device on a first of the plurality of rigid links, and a second electronic device on a second of the plurality of rigid links; and an electrical communication pathway between first electronic device and the second electronic device and through at least a portion of one of the number of pivot joints.

Example 2 can include or use, or can optionally be combined with the subject matter of Example 1, to optionally include or use one or more electrically conductive gears that can be coupled to each of a first rigid link and a second rigid link, wherein each electrically conductive gear can have a central gear axis about which the gear is allowed to rotate; and the one or more electrically conductive gears of the first rigid link can be sized and shaped to intermesh with the one or more electrically conductive gears of the second rigid link.

Example 3 can include or use, or can optionally be combined with the subject matter of one or any combination of Examples 1 or 2 to optionally include or use one or more electrically conductive gears of a first rigid link that can each be electrically isolated from the other electrically conductive gears that are coupled to the first rigid link.

Example 4 can include or use, or can optionally be combined with the subject matter of one or any combination of Examples 1 through 3 to optionally include or use first and second rigid links that can have a cylindrical passage, wherein the cylindrical passage can have a central passage axis that can be collinear with the central gear axis; additionally, the cylindrical passage can be sized and shaped to receive a connector.

Example 5 can include, or can optionally be combined with the subject matter of one or any combination of Examples 1 through 4 to include or use that reception of a connector within a cylindrical passage can physically couple first and second rigid links and establish an electrical communication pathway between a first electronic device and a second electronic device.

Example 6 can include, or can optionally be combined with the subject matter of one or any combination of Examples 1 through 5 to include or use that a first or second electronic device can include a printed circuit board.

Example 7 can include, or can optionally be combined with the subject matter of one or any combination of Examples 1 through 6 to include or use that a first or second electronic device can be selected from the group consisting of a processor, battery, accelerometer, gyroscope, inertial measurement unit, global positioning system receiver, cellular radio, Bluetooth radio, solid state memory, random access memory, microphone, speaker, induction coil, heart rate sensor, blood pressure sensor, temperature sensor, barometric pressure sensor, photosensor, liquid sensor, diode, and a display.

Example 8 can include, or can optionally be combined with the subject matter of one or any combination of Examples 1 through 7 to include or use that pivot joints can be coupled with a seal that can provide an interference fit with a connector when the seal is coupled with the connector.

Example 9 can include, or can optionally be combined with the subject matter of one or any combination of Examples 1 through 8 to include or use a first electronic device and a second electronic device that can be sub-components of an electronic system.

Example 10 can include, or can optionally be combined with the subject matter of one or any combination of Examples 1 through 9 to include or use sub-components that can be in wireless communication.

Example 11 can include, or can optionally be combined with the subject matter of one or any combination of Examples 1 through 10 to include or use first and second electronic devices that can be in wireless communication.

Example 12 can include, or can optionally be combined with the subject matter of one or any combination of Examples 1 through 11 to include or use rigid links that can be components of a piece of jewelry.

Example 13 can include, or can optionally be combined with the subject matter of one or any combination of Examples 1 through 12 to include or use a piece of jewelry that can be a watch.

Example 14 can include or use a method for modifying a wearable electronic device, comprising: decoupling a first rigid link from a second rigid link; placing the first rigid link within physical proximity of a third rigid link; coupling the first rigid link with the third rigid link, wherein the coupling of the first rigid link with the third rigid link establishes an electrical communication pathway between a first electronic device and a second electronic device and through at least a portion of a pivot joint of the first or third rigid link.

Example 15 can include or use, or can optionally be combined with the subject matter of Example 14, to optionally include or use a third rigid link that can be a replacement for the second rigid link.

Example 16 can include or use, or can optionally be combined with the subject matter of one or any combination of Examples 14 or 15 to optionally include or use a third rigid link that can be added to increase functionality of the wearable electronic device.

Example 17 can include or use, or can optionally be combined with the subject matter of one or any combination of Examples 14 through 16 to optionally include or use a first or second electronic device that can be selected from the group consisting of a processor, battery, accelerometer, gyroscope, inertial measurement unit, global positioning system receiver, cellular radio, Bluetooth radio, solid state memory, random access memory, microphone, speaker, induction coil, heart rate sensor, blood pressure sensor, temperature sensor, barometric pressure sensor, photosensor, liquid sensor, diode, and a display.

Example 18 can include or use, or can optionally be combined with the subject matter of one or any combination of Examples 14-17 to optionally include or use coupling a first rigid link with a third rigid link that can include intermeshing one or more electrically conductive gears of the first rigid link with one or more electrically conductive gears of the third rigid link.

Example 19 can include or use a flexible band wearable electronic device, comprising: a plurality of rigid links; a number of pivot means coupling the plurality of rigid links together; a first electronic device on a first of the plurality of rigid links, and a second electronic device on a second of the plurality of rigid links; and a communication pathway means between first electronic device and the second electronic device and through at least a portion of one of the number of pivot means.

Example 20 can include or use, or can optionally be combined with the subject matter of Example 19, to optionally include or use a first or second electronic device that can be selected from the group consisting of a processor, battery, accelerometer, gyroscope, inertial measurement unit, global positioning system receiver, cellular radio, Bluetooth radio, solid state memory, random access memory, microphone, speaker, induction coil, heart rate sensor, blood pressure sensor, temperature sensor, barometric pressure sensor, photosensor, liquid sensor, diode, and a display.

Example 21 can include or use, or can optionally be combined with the subject matter of one or any combination of Examples 19 or 21 to optionally include or use a first or second electronic device that can include a printed circuit board.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A flexible band wearable electronic device, comprising:
a plurality of rigid links, including a first rigid link and a second rigid link, wherein the first rigid link and the second rigid link each include a passage configured to receive a connector;
a first set of electrically conductive gears coupled to the first rigid link, wherein each of the first set of electrically conductive gears are electrically isolated;
a second set of electrically conductive gears coupled to the second rigid link, wherein:
each of the second set of electrically conductive gears are electrically isolated, and
the first set of conductive gears are sized and shaped to intermesh with the second set of electrically conductive gears;
the connector configured to engage with the passages of the first rigid link and the second rigid link, wherein the connector is configured to couple the first rigid link with the second rigid link, the first rigid link and the second rigid link pivot about the connector at the passages, and the coupling of the first rigid link with the second rigid link intermesh the first set of electrically conductive gears with the second set of electrically conductive gears;
a first electronic device included in the first rigid link, and a second electronic device included in the second rigid link; and
wherein the intermeshing of the first set of electrically conductive gears with the second set of electrically conductive gears establishes a plurality of isolated electrical communication pathways between the first electronic device and the second electronic device, and the coupling of the connector with the first rigid link and the second rigid link:
establishes an additional isolated electrical communication pathway between the first electronic device and the second electronic device, and
maintains the intermeshing of the first set of electrically conductive gears with the second set of electrically conductive gears.

2. The flexible band wearable electronic device of claim 1, wherein each of the first set of electrically conductive gears includes a central gear axis, and the central gear axis of each of the first set of electrically conductive gears are collinear.

3. The flexible band wearable electronic device of claim 2, wherein the passage of the first rigid link is aligned with the central gear axis of first set of electrically conductive gears.

4. The flexible band wearable electronic device of claim 1, wherein the connector is removable by a user to facilitate the interchanging of the first rigid link or the second rigid link with a third rigid link.

5. The flexible band wearable electronic device of claim 1, wherein the connector includes a plurality of isolated channels configured to allow a plurality of isolated electrical signals to transmit through the connector.

6. The flexible band wearable electronic device of claim 1, wherein the first or second electronic device includes a printed circuit board.

7. The flexible band wearable electronic device of claim 1, wherein the first or second electronic device is selected from the group consisting of a processor, battery, accelerometer, gyroscope, inertial measurement unit, global positioning system receiver, cellular radio, Bluetooth radio, solid state memory, random access memory, microphone, speaker, induction coil, heart rate sensor, blood pressure sensor, temperature sensor, barometric pressure sensor, photosensor, liquid sensor, diode, and a display.

8. The flexible band wearable electronic device of claim 1, wherein the the connector is coupled with a seal that provides an interference fit with the connector when the seal is coupled with the connector.

9. The flexible band wearable electronic device of claim 1, wherein the first electronic device and the second electronic device are sub-components of an electronic system.

10. The flexible band wearable electronic device of claim 9, wherein the sub-components are in wireless communication.

11. The flexible band wearable electronic device of claim 1, wherein the first and second electronic devices are in wireless communication.

12. The flexible band wearable electronic device of claim 1, wherein the rigid links are components of a piece of jewelry.

13. The flexible band wearable electronic device of claim 12, wherein the piece of jewelry is a watch.

14. A method for modifying a wearable electronic device, comprising:
decoupling a first rigid link from a second rigid link, wherein the decoupling includes:
removing a connector from the first rigid link and the second rigid link, wherein the connector is configured to engage with a first passage of the first rigid link and a second passage of the second rigid link, and
demeshing a first set of electrically conductive gears of the first rigid link from a second set of electrically conductive gears of the second rigid link;
placing the first rigid link within physical proximity of a third rigid link; and
coupling the first rigid link with the third rigid link, wherein the coupling of the first rigid link with the third rigid link includes:
intermeshing a third set of electrically conductive gears of the third link with the first set of electrically conductive gears,
coupling the connector with the first passage and a third passage of the third rigid link, wherein the first rigid link and the third rigid link are configured to pivot about the connector at the first passage and the third passage, and
wherein the intermeshing of the first set of electrically conductive gears with the third set of electrically conductive gears establishes a plurality of isolated electrical communication pathways between a first electronic device and a second electronic device, and the coupling of the connector with the first rigid link and the third rigid link:
establishes an additional isolated electrical communication pathway between the first electronic device and the second electronic device, and
maintains the intermeshing of the first set of electrically conductive gears with the third set of electrically conductive gears.

15. The method for modifying a wearable electronic device of claim 14, wherein the third rigid link is a replacement for the second rigid link.

16. The method for modifying a wearable electronic device of claim 14, wherein the third rigid link is added to increase functionality of the wearable electronic device.

17. The method for modifying a wearable electronic device of claim 14, wherein the first or second electronic device is selected from the group consisting of a processor, battery, accelerometer, gyroscope, inertial measurement unit, global positioning system receiver, cellular radio, Bluetooth radio, solid state memory, random access memory, microphone, speaker, induction coil, heart rate sensor, blood pressure sensor, temperature sensor, barometric pressure sensor, photosensor, liquid sensor, diode, and a display.

18. The method for modifying a wearable electronic device of claim 14, wherein coupling the first rigid link with the third rigid link includes intermeshing one or more electrically conductive gears of the first rigid link with one or more electrically conductive gears of the third rigid link.

\* \* \* \* \*

UNITED STATES PATENT AND TRADEMARK OFFICE
CERTIFICATE OF CORRECTION

PATENT NO. : 10,228,725 B2
APPLICATION NO. : 15/282633
DATED : March 12, 2019
INVENTOR(S) : Albers et al.

Page 1 of 1

It is certified that error appears in the above-identified patent and that said Letters Patent is hereby corrected as shown below:

In the Claims

In Column 11, Line 52, in Claim 8, delete "the the" and insert --the-- therefor

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*